United States Patent
Magovern et al.

[11] Patent Number: 6,120,431
[45] Date of Patent: Sep. 19, 2000

[54] METHOD FOR ASSISTING STYSTOLIC AND DIASTOLIC CARDIAC FUNCTION

[75] Inventors: James A. Magovern; Dennis R. Trumble, both of Pittsburgh, Pa.

[73] Assignee: Allegheny-Singer Research Institute, Pittsburgh, Pa.

[21] Appl. No.: 08/818,570

[22] Filed: Mar. 14, 1997

[51] Int. Cl.[7] ........................................ A61M 1/12
[52] U.S. Cl. ................................... 600/17; 623/3
[58] Field of Search .................. 128/DIG. 3; 600/16.18; 623/3

[56] References Cited

U.S. PATENT DOCUMENTS

| | | | |
|---|---|---|---|
| 4,536,893 | 8/1985 | Parravicini | 623/3 |
| 5,131,905 | 7/1992 | Grooters | 600/16 |
| 5,169,381 | 12/1992 | Synders | 600/16 |
| 5,256,132 | 10/1993 | Synders | 600/16 |
| 5,453,076 | 9/1995 | Kiyota et al. | 600/18 |
| 5,498,228 | 3/1996 | Royalty et al. | 600/16 |

*Primary Examiner*—William E. Kamm
*Assistant Examiner*—George R. Evanisko
*Attorney, Agent, or Firm*—Ansel M. Schwartz

[57] ABSTRACT

The present invention pertains to an apparatus for assisting a patient's heart operation. The apparatus comprises a mechanism for expanding and collapsing a right ventricle free wall of a heart of a patient. The apparatus also comprises a mechanism for powering the expanding and collapsing mechanism. The powering mechanism is in communication with the expanding and collapsing mechanism. The present invention pertains to a method for assisting operation of a patient's heart. The method comprises the steps of expanding a balloon placed between a right ventricle free wall and a septum of a patient such that right ventricular compression is achieved during cardiac systole. Then there is the step of collapsing the balloon during cardiac diastole.

7 Claims, 2 Drawing Sheets

METHOD FOR ASSISTING STYSTOLIC AND DIASTOLIC CARDIAC FUNCTION

FIELD OF THE INVENTION

The present invention is related to assisting the operation of a patient's heart. More specifically, the present invention is related to assisting the right ventricle (RV) function of a patient.

BACKGROUND OF THE INVENTION

When pharmacological agents are unable to improve RV function, surgeons must rely on mechanical means to restore blood flow to the pulmonary circulation and left ventricle. Current options for mechanical assist include: centrifugal pumps; positive displacement pumps; and right-sided balloon counterpulsation. The drawback common to all these mechanisms is that they require invasive, time-consuming procedures to secure requisite cannulae and/or anastomoses to the pulmonary artery (unlike IABP assist of the left ventricle which can be positioned and retracted through a femoral artery cutdown).

The present invention was developed to provide a quick and simple means to assist the failing right ventricle. The inspiration for the present invention was the technique of cardiopulmonary resuscitation, in which the chest wall is physically compressed to cause ejection of blood from an arrested heart. The idea was to use expansion/deflation of a balloon within the chest cavity to achieve a similar result. It was believed intuitively that this approach would be more successful for RV assistance because the pulmonary circulation is a low resistance circuit that operates at a pressure 25% of that for the systemic circulation.

The present invention, unlike those currently available, allows minimally-invasive RV assist through a small subxiphoid incision. The expanding and collapsing mechanism can be rapidly deployed and is positioned in the anterior mediastinum. Expanding and collapsing mechanism removal can be effected by simply retracting the balloon from the pericardial space in a manner similar to removing a chest tube.

A discussion of RV assist devices and the treatment of RV failure appears in a review article by R. Higgins and J. Elefteriades titled "Right Ventricular Assist Devices and the Surgical Treatment of Right Ventricular Failure", *Cardiology Clinics,* Volume 10, Number 1, Feb. 1992, incorporated by reference herein.

Some characteristics which separate the present invention from other compression devices or RV assist devices currently on the market are its:

low cost mechanical simplicity ease of use (esp. insertion and removal)

does not encircle the heart or directly compress the LV and designed to assist the RV with LV assistance as a secondary consideration.

SUMMARY OF THE INVENTION

The present invention pertains to an apparatus for assisting a patient's heart function. The apparatus comprises a mechanism for expanding and collapsing a right ventricle free wall of a heart of a patient. The apparatus also comprises a mechanism for powering the expanding and collapsing mechanism. The powering mechanism is in communication with the expanding and collapsing mechanism.

The present invention pertains to a method for assisting function of a patient's heart. The method comprises the steps of expanding a balloon placed between a right ventricle free wall and a septum of a patient such that right ventricular compression is achieved during cardiac systole. Then there is the step of collapsing the balloon during cardiac diastole.

BRIEF DESCRIPTION OF THE DRAWINGS

In the accompanying drawings, the preferred embodiment of the invention and preferred methods of practicing the invention are illustrated in which.

DESCRIPTION OF THE PREFERRED EMBODIMENT

Figure 1:
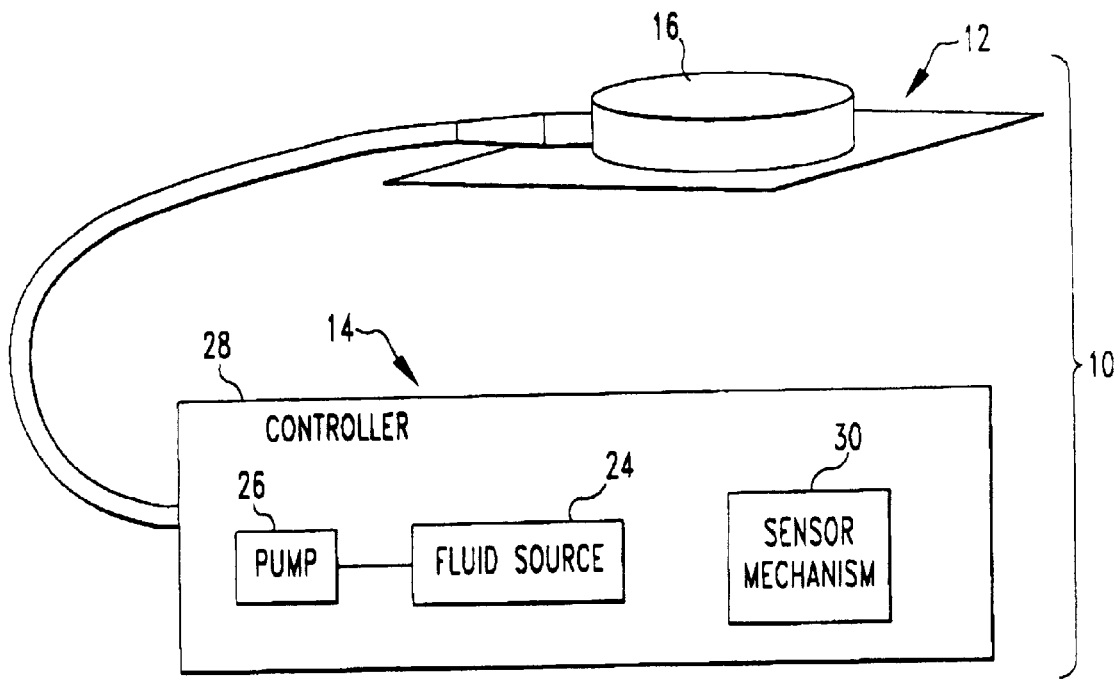
FIG. 1 is a schematic representation of an apparatus of the present invention.
Figure 2:
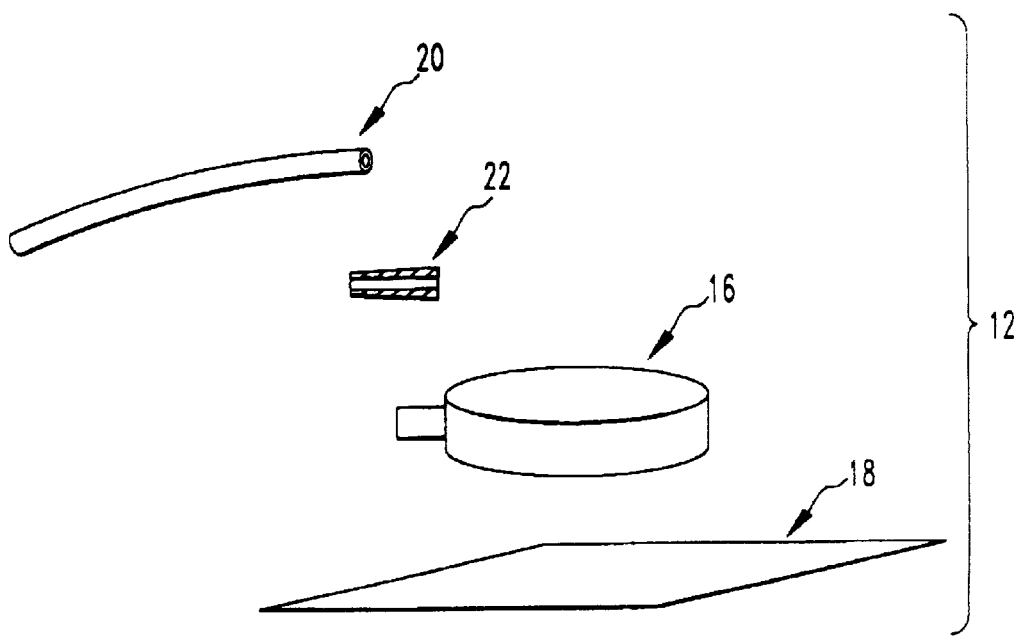
FIG. 2 is a schematic representation of an exploded view of an expanding and connecting mechanism of FIG. 1.
Figure 3:
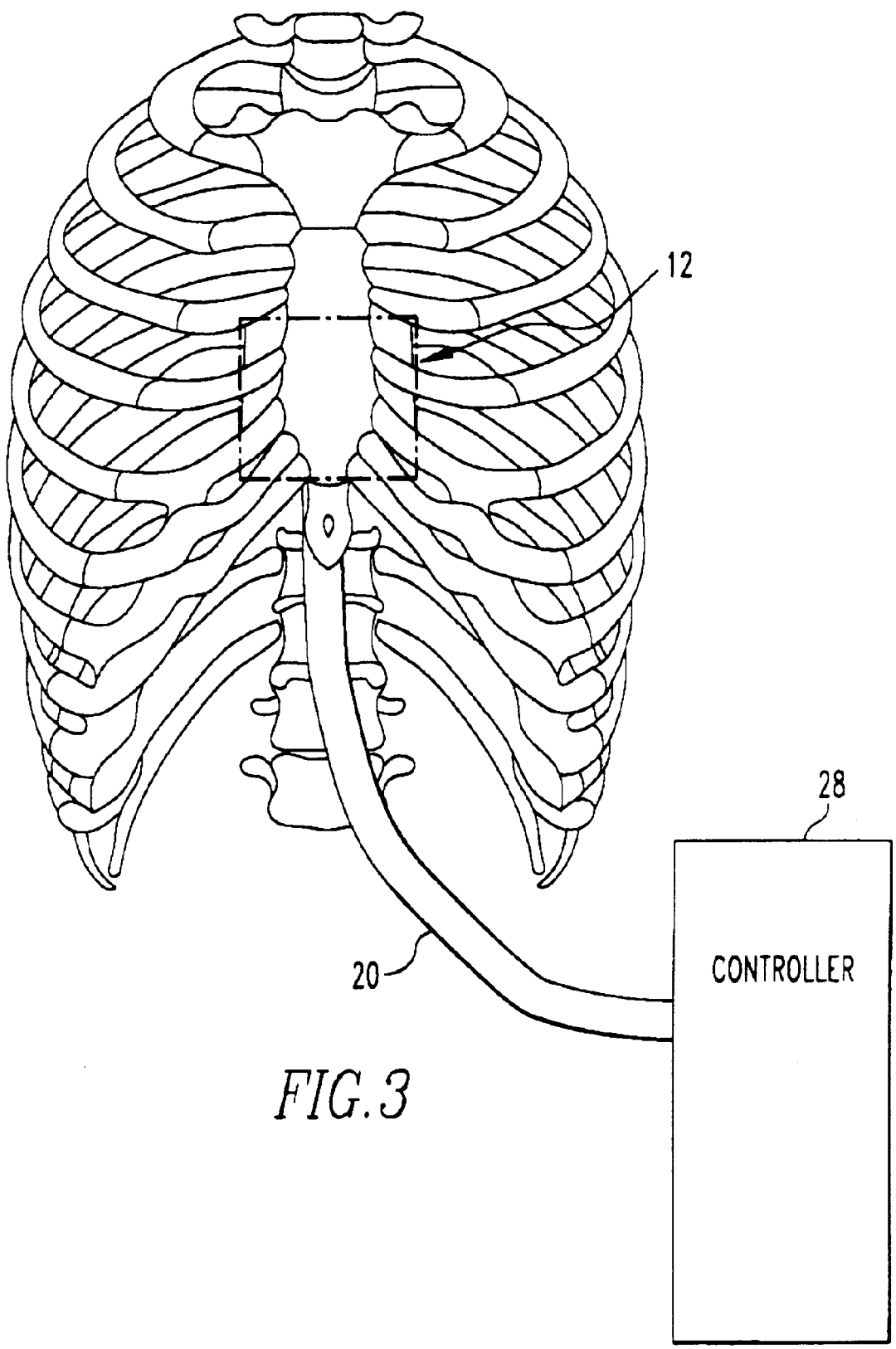
FIG. 3 is a schematic representation of the apparatus in place on a portion of a patient.

Referring now to the drawings wherein like reference numerals refer to similar or identical parts throughout the several views, and more specifically to FIG. 1 thereof, there is shown an apparatus 10 for assisting a patient's heart function. The apparatus 10 comprises a mechanism 12 for expanding and collapsing a right ventricle free wall of a heart of a patient. The apparatus 10 also comprises a mechanism 14 for powering the expanding and collapsing mechanism 12. The powering mechanism 14 is in communication with the expanding and collapsing mechanism 12.

Preferably, the expanding and collapsing mechanism 12 is adapted to be inserted or implanted into the patient. The expanding and collapsing mechanism 12 preferably includes an expandable and flexible balloon 16. Preferably, the expandable and collapsing mechanism 12 includes a balloon backing 18 upon which the balloon 16 is attached and that causes the balloon 16 to expand away from the backing 18 as it expands. The balloon 16 is adapted to be attached to the patient and to stabilize the balloon 16 in place. The expandable and collapsing mechanism 12 preferably includes a pneumatic drive line 20 which delivers fluid to or removes fluid from the balloon 16 to expand or collapse it. Preferably, the expanding and collapsing mechanism 12 includes a drive line connector 22 for connecting the drive line 20 to the balloon 16. The drive line connector 22 is connected to the drive line 20 and the balloon 16.

The powering mechanism 12 preferably includes a fluid source 24, and a pump 26 connected to the fluid source 24 and to the drive line 20 for pumping fluid into the balloon 16 to expand the balloon 16 and pumping fluid out of the balloon 16 to collapse the balloon 16. Preferably, the powering mechanism 12 includes a controller 28 for controlling when the pump 26 pumps fluid into or out of the balloon 16. The controller 28 is connected to the pump 26. The powering mechanism 12 preferably includes a sensor mechanism 30 adapted for connection to a patient for sensing a patient's heart rate. The sensor mechanism 30 is connected to the controller 28 for providing a signal to the controller 28 corresponding to the patient's heart so the controller 28 can cause the pump 26 to operate in synchrony with the heart of the patient.

The present invention pertains to a method for assisting function of a patient's heart. The method comprises the steps of expanding a balloon 16 placed between a right ventricle free wall and a sternum of a patient such that right ventricular compression is achieved during cardiac systole. Then there is the step of collapsing the balloon 16 during cardiac diastole.

The expanding step preferably includes the step of pumping fluid into the balloon 16. Preferably, before the expanding step there is the step of placing a balloon 16 having a balloon backing 18 between the right ventricle free wall and the sternum. After the placing step there is preferably the step of fixing the balloon backing 18 to the surface of the sternum. Preferably, before the expanding step there is the step of synchronizing the expansion and compression of the balloon 16 with the cardiac systole and cardiac diastole of the heart of the patient.

In the operation of the preferred embodiment, the expanding and collapsing mechanism 12 comprises four (4) components which are as follows:

1) a pneumatic drive line 20;

2) a drive line connector 22;

3) an expandable, compliant balloon 16;

and 4) a firm balloon-backing 18;

A pneumatic drive controller 26 (preferably a modified IABP pump console system 83 available from Datascope Corp. See system 83 operating instructions, incorporated by reference herein) is required to actuate the expanding and collapsing mechanism 12. Console modifications required for expanding and collapsing mechanism 12 actuation involve: 1) increasing the volume of fluid delivered to the balloon 16; and 2) synchronizing balloon 16 inflation with cardiac systole. The first modification can be readily achieved by placing a second safety chamber in parallel with the standard 40 cc safety chamber such that maximum fluid volume delivery is doubled to 80 cc. The second modification is achieved by simply setting the drive console's inflation delay switch to the "out" position, thereby disabling the automatic delay function and allowing balloon 16 inflation to occur immediately following QRS detection.

Component function is as follows:

Pneumatic drive line 20: Provides means for delivering compressed gas (usually Nitrogen) from the drive console to the balloon 16. The drive line 20 can be any hollow conduit (roughly ¼" inner diameter) that is both flexible and non-compliant. Note: positive pressure is generated within the drive line 20 during the inflation phase (cardiac systole) and negative pressure is generated during balloon 16 deflation (cardiac diastole).

Drive line connector 22: Provides a stable interface between the pneumatic drive line 20 and the balloon 16.

Expandable balloon 16: Expands and collapses in synchrony with the heart to move the right ventricular free wall toward the septum and thereby propel blood into the pulmonary artery. Balloon 16 expansion may also serve to increase intra-thoracic pressure which will provide an additional force for increasing ejection of blood from the heart. Active deflation may also aid diastolic filling of the heart.

Firm balloon-backing 18: Causes the balloon 16 to expand away from the backing 18 and toward the heart. Also provides a means to suture the device into place should proper device positioning prove difficult to maintain.

The expanding and collapsing mechanism 12 is designed to assist right ventricular function by displacing the RV free wall toward the cardiac septum (via direct compression). This action causes blood to be propelled through the pulmonary valve into the pulmonary circulation. Cardiac assist is achieved by expanding a balloon 16 placed between the RV free wall and the septum such that RV compression is achieved during cardiac contraction (i.e., systole).

A certain amount of left ventricular augmentation may also be achieved via the following mechanisms:

stabilization of the intraventricular septum;

rapid increase and decrease in intrathoracic pressure, which will alternately aid ejection and filling of the left and right ventricles;

LV compression against the back of the thoracic cage.

The expanding and collapsing mechanism 12 may be placed on the epicardial surface during open-heart surgery or placed external to the pericardium via a small subxiphoid incision. In the former case, the expanding and collapsing mechanism 12 can be sutured to the epicardial surface or to the pericardium using the backing 18 such that the balloon 16 expands toward the heart. In the latter case, the balloon 16 is inserted into the space between the sternum and RV free wall (i.e., anterior mediastinum) such that the balloon 16 lies between the backing 18 and the cardiac surface. Expanding and collapsing mechanism 12 insertion occurs with the balloon 16 actively deflated (by applying a small negative pressure) and is expanded in the anterior mediastinum. A passive fixation mechanism (e.g., sutures, barbed felt backing, etc.) can be used to keep the device attached to the posterior surface of the sternum.

The expanding and collapsing mechanism 12 is operated pneumatically by moving a known volume of gas into and out of the balloon 16 in synchrony with cardiac contraction. The preferred means of actuation is an intra-aortic balloon pump (IABP) console modified to move 65 cc's of gas into the expanding and collapsing mechanism during systole and out during diastole (under a slight vacuum). Cardiac synchronization is achieved by sending the patient's ECG signal from a sensor mechanism such as standard ECG sensor terminals on the patient to the drive console, where the QRS complex triggers balloon 16 inflation. Sensing circuitry within the drive console amplifies the cardiac signal and sends it to a comparator which activates balloon inflation when sensed voltage levels rise above some preset value. The "trigger level" can be modified as needed by adjusting the drive console's sensitivity setting. Timing of balloon 16 deflation can be controlled by adjusting the "delay" setting of the drive console. Optimum timing is achieved by adjusting the driver settings to obtain optimum systemic blood pressure and pulmonary artery pressure tracings. Another parameter which may be used to optimize device performance is PA blood flow/velocity (monitored non-invasively via echocardiogram).

The expanding and collapsing mechanism 12 is fabricated using silicone balloons (65 cc maximum volume), standard IABP pressure tubing (5/16" OD; 3/16 " ID), Teflon felt, and ¼"-to-⅜" tubing connectors. Balloons are roughly 5 cm in diameter and 2 cm high, with a single lateral convolution to aid vertical expansion. The balloon 16 is attached to the tubing connector (⅜" end) using UV-curable adhesive or other means to form an air-tight seal. Silicone adhesive is then used to secure the balloon 16 to the Teflon felt backing. Finally, the pressure tubing is pushed over the tubing connector (no adhesive required) to complete the expanding and collapsing mechanism's manufacture. For infants, about 20 cc of gas can be used; children, about 30–40 cc of gas can be used and so on based on the size of the patient.

The size of the expanding and collapsing mechanism 12 would change also according to the size of the patient.

Note that a stiff mesh screen or other interference materials may be placed over the balloon side of the tubing connector 22 prior to assembly in order to prevent the balloon 16 from being sucked into the lumen of the connector 22 during active deflation.

The apparatus 10 is typically considered for use over a period of one week to one month. The apparatus 10 can be used for a shorter time or a longer time. However, the longer the time the apparatus 10 is used, the more likely infection can occur and so appropriate steps must be taken to avoid such infection, as is well known in the art.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method for assisting function of a patient's heart comprising the steps of:

placing a balloon having a balloon backing between a right ventricular free wall and a sternum of a patient, wherein the balloon only contacts the right ventricular free wall opposite the sternum during expansion of the balloon;

expanding the balloon placed between a right ventricular free wall and the sternum of the patient with positive pressure from a powering mechanism connected to the balloon such that right ventricular compression is achieved during cardiac systole by direct compression of the right ventricle by the balloon; and collapsing the balloon during cardiac diastole with negative pressure from the powering mechanism such that diastolic filling of the heart is assisted.

2. A method as described in claim 1 including after the placing step there is the step of fixing the balloon backing to the surface of the sternum.

3. A method as described in claim 2 including after the placing step, there is the step of synchronizing the expansion and compression of the balloon with the cardiac systole and cardiac diastole of the heart of the patient.

4. A method as described in claim 3 wherein the expanding step includes the step of pumping fluid into the balloon.

5. A method for assisting function of a patient's heart comprising the steps of:

placing a balloon having a balloon backing between a right ventricular free wall and a sternum of a patient, wherein the balloon only contacts the right ventricular free wall opposite the sternum during expansion of the balloon;

expanding the balloon placed between a right ventricular free wall and the sternum of a patient such that right ventricular compression is achieved during cardiac systole; and collapsing the balloon during cardiac diastole.

6. A method as described in claim 5 including before the placing step, there is the step of making a sub-xiphoid incision in the patient.

7. A method as described in claim 6 wherein the placing step includes the step of placing the balloon through the incision.

* * * * *